(12) United States Patent  
Kondo (10) Patent No.: US 7,659,654 B2  
(45) Date of Patent: Feb. 9, 2010

(54) PIEZOELECTRICS OSCILLATOR, SENSOR, AND MULTI-SENSOR (75) Inventor: Takayuki Kondo, Chino (JP)

(73) Assignee: Seiko Epson Corporation (JP)

( * ) Notice: Subject to any disclaimer, the term of this patent is extended or adjusted under 35 U.S.C. 154(b) by 126 days.

(21) Appl. No.: 12/052,776

(22) Filed: Mar. 21, 2008

(65) Prior Publication Data  
US 2008/0229829 A1 Sep. 25, 2008

(30) Foreign Application Priority Data  
Mar. 22, 2007 (JP) ............................. 2007-074126

(51) Int. Cl.  
H01L 41/08 (2006.01)

(52) U.S. Cl. .................. 310/330; 310/331; 310/332; 310/328; 310/367; 310/324; 73/862

(58) Field of Classification Search ................. 310/328, 310/330–332, 324; 73/862  
See application file for complete search history.

(56) References Cited

U.S. PATENT DOCUMENTS

| 5,852,229 | A * | 12/1998 | Josse et al. ................. 73/24.06 |
| 6,263,734 | B1* | 7/2001 | Fujii et al. ................ 73/514.34 |
| 6,886,405 | B2* | 5/2005 | Yang ........................ 73/514.32 |
| 7,134,319 | B2* | 11/2006 | Liu ............................ 73/31.06 |
| 7,253,488 | B2* | 8/2007 | Zhan et al. .................. 257/414 |
| 7,388,445 | B2* | 6/2008 | Ohshima et al. ............. 331/158 |
| 7,425,749 | B2* | 9/2008 | Hartzell et al. .............. 257/414 |
| 7,449,758 | B2* | 11/2008 | Axelrod et al. .............. 257/415 |
| 7,497,133 | B2* | 3/2009 | Shih et al. ............. 73/862.639 |
| 2004/0235267 | A1* | 11/2004 | Sheats et al. ................ 438/455 |
| 2005/0262943 | A1* | 12/2005 | Claydon et al. .............. 73/579 |
| 2007/0278600 | A1* | 12/2007 | Zhan et al. .................. 257/415 |
| 2007/0287233 | A1* | 12/2007 | Zhan et al. .................. 438/149 |
| 2008/0022755 | A1 | 1/2008 | Shinbo et al. |

FOREIGN PATENT DOCUMENTS

| JP | 48-028188 | 4/1973 |
| JP | 56-160016 | 4/1980 |
| JP | 10-075120 | 3/1998 |
| JP | 11-014525 | 1/1999 |
| JP | 2004-264255 | 9/2004 |
| JP | 2005-166912 | 6/2005 |
| WO | WO2006-006587 | 1/2006 |

* cited by examiner

Primary Examiner—J. SanMartin  
(74) Attorney, Agent, or Firm—Harness, Dickey & Pierce, P.L.C.

(57) ABSTRACT

A piezoelectric oscillator includes: a piezoelectric substrate having at least a vibrating part and a base part; an excitation electrode formed on the vibrating part; and an oscillation circuit formed on the base part. In the piezoelectric oscillator, the oscillation circuit includes a thin film transistor made of one of polysilicon and monocrystalline silicon and is coupled to the excitation electrode.

13 Claims, 5 Drawing Sheets

PIEZOELECTRICS OSCILLATOR, SENSOR, AND MULTI-SENSOR

The entire disclosure of Japanese Patent Application No. 2007-074126, filed Mar. 22, 2007 is expressly incorporated by reference herein.

BACKGROUND

1. Technical Field

The present invention relates to a piezoelectric oscillator, and a sensor and a multi-sensor that employ a piezoelectric oscillator.

2. Related Art

In recent years, as accompanied with miniaturization of electronic devices, miniaturization of piezoelectric oscillators such as a crystal oscillator mounted on electronic devices has been increasingly required.

In order to meet such requirement, JP-A-10-75120, as a first example, discloses a crystal oscillator that stores a crystal vibrator and an electronic component constituting an oscillation circuit in one container.

In addition, miniaturization of sensors employing a piezoelectric oscillator has been required. For the miniaturization thereof, JP-A-2004-264255, as a second example, discloses a mass measuring chip in which a piezoelectric resonator element and an IC chip are bonded to one flat plate in an electrically connecting fashion to each other. The mass measuring chip detects a specific substance adsorbed by the piezoelectric resonator element in accordance with an amount of the frequency change.

However, in the crystal oscillator (hereinafter, referred to as a piezoelectric oscillator) disclosed in the first example, even though the crystal vibrator (hereinafter, referred to as a piezoelectric substrate) and the electronic component constituting the oscillation circuit are stored in one container (hereinafter, referred to as a package), the piezoelectric substrate and the electronic component are stored in separate cavities within the package. That is, in this structure, the package needs a space for storing the piezoelectric substrate and a space for storing the electronic component separately therein, making the further miniaturization difficult.

Further, since the electronic component is a discrete component and is provided in a great number, the number of manufacturing steps increases to degrade the productivity. In addition, since the discrete component is commonly thick, it is hard to thin the crystal oscillator.

Furthermore, a circuit pattern for wiring a plurality of discrete components becomes complex so as to generate electromagnetic coupling between circuit patterns, deteriorating the performance of the oscillator disadvantageously.

The mass measuring chip (hereinafter, referred to as a sensor) disclosed in the second example has such structure that the piezoelectric resonator element and the IC chip constituting the oscillation circuit are bonded separately to the flat plate, so that the structure hardly satisfies suitable manufacturing efficiency. In addition, the sensor mounts the piezoelectric resonator element on the flat plate, being hard to be thinned.

SUMMARY

An advantage of the present invention is to provide a piezoelectric oscillator, a sensor, and a multi-sensor that have excellent productivity. Another advantage is to provide a compact piezoelectric oscillator, a compact sensor, and a compact multi-sensor.

A piezoelectric oscillator according to a first aspect of the invention includes: a piezoelectric substrate having at least a vibrating part and a base part; an excitation electrode formed on the vibrating part; and an oscillation circuit formed on the base part. In the piezoelectric oscillator, the oscillation circuit includes a thin film transistor made of one of polysilicon and monocrystalline silicon and is coupled to the excitation electrode.

Since the piezoelectric oscillator is provided with the excitation electrode and the oscillation circuit on its piezoelectric substrate as above, the piezoelectric substrate and the oscillation circuit are unified, improving the space efficiency. Thus the piezoelectric oscillator can be miniaturized. In addition, in the piezoelectric oscillator, the piezoelectric substrate and the oscillation circuit are unified and thus the number of manufacturing steps is reduced due to the reduced number of components, improving the productivity.

Further, because of the unification of the piezoelectric substrate and the oscillation circuit, the excitation electrode and the oscillation circuit are coupled at a short distance. Therefore, electromagnetic interference between the connecting patterns is suppressed. Thus the performance of the piezoelectric oscillator can be enhanced.

In the piezoelectric oscillator of the first aspect, the piezoelectric substrate may be an AT cut quartz substrate.

Since the piezoelectric substrate is the AT cut quartz substrate, the piezoelectric oscillator has small frequency change with respect to the temperature change of the surroundings and the frequency can be increased by thinning the thickness of the substrate. Thus a high frequency oscillator having a desirable temperature property can be easily realized.

In the piezoelectric oscillator of the first aspect, the oscillation circuit and the excitation electrode may be formed on a first main surface of the piezoelectric substrate, and a common electrode may be formed on a second main surface in an opposed manner to the excitation electrode.

Since the oscillation circuit and the excitation electrode are formed on the first main surface of the piezoelectric substrate in the piezoelectric oscillator, the oscillation circuit and the excitation electrode are coupled by single-sided wiring, facilitating the wiring.

The oscillation circuit and the excitation electrode are coupled at a short distance by the single-sided wiring, so that the electromagnetic interference between the wiring patterns is suppressed, being able to enhance performance of the piezoelectric oscillator.

In the piezoelectric oscillator of the first aspect, the vibrating part of the piezoelectric substrate may have a recess on the first main surface.

Since the vibrating part of the piezoelectric substrate has a recess in the piezoelectric oscillator and thus the thickness of the inside of the vibrating part can be thinned without changing the thickness of the periphery of the vibrating part, the frequency can be increased while maintaining the strength of the piezoelectric substrate.

A sensor according to a second aspect of the invention includes: a piezoelectric substrate having at least a vibrating part and a base part; an excitation electrode formed on the vibrating part; an oscillation circuit formed on the base part; and a sensitive film formed on the vibrating part and increasing a mass thereof by adsorbing a selected substance. In the sensor, the oscillation circuit includes a thin film transistor made of one of polysilicon and monocrystalline silicon and is coupled to the excitation electrode.

The excitation electrode and the oscillation circuit are formed on the piezoelectric substrate and the sensitive film is formed on the vibrating part of the piezoelectric substrate in the sensor as above. In this structure, the mass increase of the sensitive film due to the adsorption of the selected substance changes the frequency of the vibrating part, so that the selected substance can be detected. The excitation electrode, the oscillation circuit, and the sensitive film are formed on the piezoelectric substrate, that is, the piezoelectric substrate, the excitation electrode, the oscillation circuit, and the sensitive film are unified. Thus the space efficiency is improved and the sensor can be miniaturized.

In addition, in the sensor, the piezoelectric substrate, the excitation electrode, the oscillation circuit, and the sensitive film are unified and thus the number of manufacturing steps is reduced due to the reduced number of components, improving the productivity.

Further, because of the unification of the piezoelectric substrate, the excitation electrode, the oscillation circuit, and the sensitive film, the excitation electrode and the oscillation circuit are coupled at a short distance, so that electromagnetic interference between the connecting patterns is suppressed. Thus the performance of the sensor can be enhanced.

In the sensor of the second aspect, the piezoelectric substrate may be an AT cut quartz substrate.

Since the piezoelectric substrate of the sensor is the AT cut quartz substrate, the frequency can be increased by reducing the thickness of the substrate and the temperature property improves. Thus the range of the frequency change due to the adsorption of the selected substance can be widened and the amount of the frequency change due to the change of the surrounding temperature can be suppressed. Therefore, the detecting sensitivity and the detecting accuracy with respect to the selected substance improve.

In the sensor of the second aspect, the oscillation circuit and the excitation electrode may be formed on a first main surface of the piezoelectric substrate, a common electrode may be formed on a second main surface in an opposed manner to the excitation electrode, and the sensitive film may be formed so as to cover the common electrode.

In this structure, the sensitive film is formed to cover the common electrode, so that the selected substance is adsorbed in a wide area. Therefore, the amount of the frequency change increases, enhancing the detecting sensitivity with respect to the selected substance.

Since the excitation electrode is formed on the first main surface provided with the oscillation circuit, the oscillation circuit and the excitation electrode are coupled by single-sided wiring in the sensor, facilitating the wiring.

The oscillation circuit and the excitation electrode are coupled at a short distance by the single-sided wiring in the sensor, so that the electromagnetic interference between the wiring patterns is suppressed, being able to enhance performance.

In the sensor of the second aspect, the vibrating part may have a recess on the first main surface.

Since the vibrating part of the piezoelectric substrate has a recess in the sensor and thus the thickness of the inside of the vibrating part can be thinned without changing the thickness of the periphery of the vibrating part, the frequency can be increased while maintaining the strength of the piezoelectric substrate. By this structure, the amount of the frequency change due to the adsorption of the selected substance increases, so that the detecting sensitivity of the sensor with respect to the selected substance can be enhanced.

The sensor of the second aspect further includes: a lid member for protecting the piezoelectric substrate. In the sensor, the lid member covers the vibrating part and a part of the oscillation circuit and is bonded to the piezoelectric substrate at least a periphery thereof, and a space formed by the lid member and the recess of the vibrating part is sealed.

According to the above, the vibrating part of the piezoelectric substrate and the oscillation circuit are covered by the lid member in the sensor. Therefore, the sensor can prevent the excitation electrode in the vibrating part and the oscillation circuit from contacting outside air, being able to prevent the performance degradation caused by oxygen or water contained in the outside air. Thus the sensor does not require a package and can be miniaturized.

The recess of the vibrating part is sealed in the sensor, so that the amount of the frequency change due to the adsorption of the substance of the outside air is not added to the amount of the frequency change due to the adsorption of the selected substance in the vibrating part. Thus the detecting accuracy with respect to the selected substance is enhanced.

Since the sensor has a space formed between the recess of the vibrating part and the lid member, the vibration in the vibrating part is not disturbed. Therefore, the sensitivity for detecting the selected substance can be maintained.

In the sensor of the second aspect, a connection terminal for inputting from and outputting to outside, of the oscillation circuit, may be exposed.

Since the connection terminal of the oscillation circuit of the sensor is exposed, it can be easily coupled to external equipment.

A multi-sensor according to a third aspect of the invention includes: a plurality of sensors of the second aspect on a large format piezoelectric substrate.

The plurality of sensors are formed on a large format piezoelectric substrate, being able to be applied as a multi-sensor. In addition, if the large format piezoelectric substrate of the multi-sensor is divided, a plurality of single sensors can be manufactured at a time, improving the productivity.

In the multi-sensor of the third aspect, each of the plurality of sensors may include the sensitive film, the sensitive film may include a plurality of sensitive films, and the plurality of the sensitive films may selectively adsorb different substances from each other.

According to the above, the plurality of sensitive films of the multi-sensor selectively adsorb different substances from each other. Thus a multi-sensor that detects a plurality of selected substances at one piezoelectric substrate and is miniaturized can be obtained.

In the multi-sensor of the third aspect, each of the plurality of sensors may include the sensitive film, the sensitive film may include a plurality of sensitive films, and at least one of the plurality of the sensitive films may selectively adsorb a substance that is different from a substance adsorbed by the remaining ones of the plurality of sensitive films.

According to the above, at least one of the plurality of the sensitive films selectively adsorbs a substance that is different from a substance adsorbed by the remaining ones of the plurality of sensitive films. Thus a multi-sensor that detects a plurality of selected substances at one piezoelectric substrate and is miniaturized can be obtained. In addition, since the plurality of sensitive films adsorb one selected substance, the detecting sensitivity with respect to one selected substance can be improved.

BRIEF DESCRIPTION OF THE DRAWINGS

The invention will be described with reference to the accompanying drawings, wherein like numbers reference like elements.

DESCRIPTION OF EXEMPLARY EMBODIMENTS

A piezoelectric oscillator and a sensor employing a piezoelectric oscillator according to embodiments of the invention will now be described with reference to the accompanying drawings.

First Embodiment

Figure 1A:
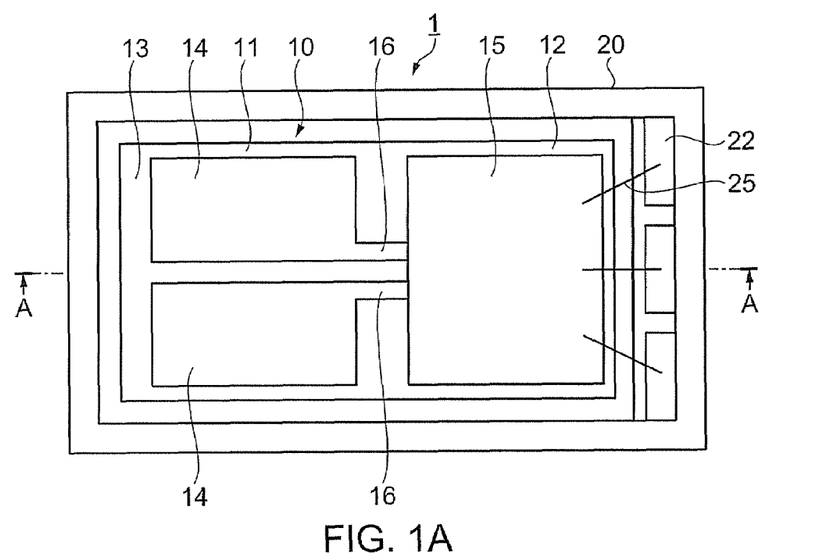
FIGS. 1A to 1C are schematic views showing a structure of a crystal oscillator according to a first embodiment of the invention.
Figure 1B:
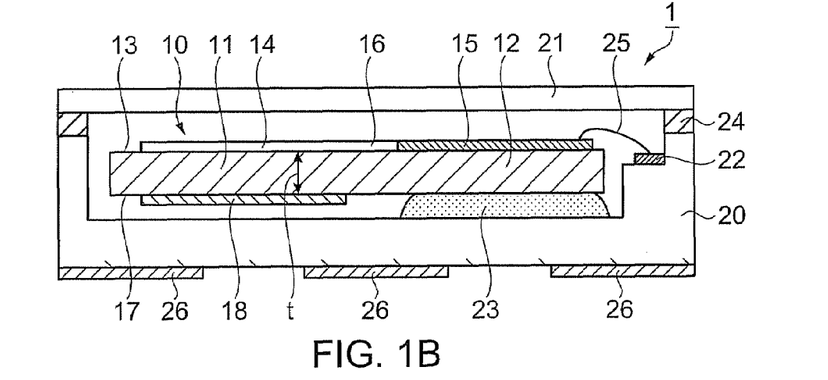
Figure 1C:
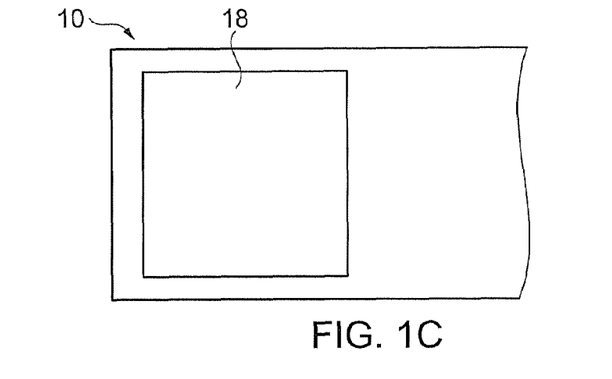

FIGS. 1A to 1C are schematic views showing a structure of a crystal oscillator as a piezoelectric oscillator according to a first embodiment of the invention. FIG. 1A is a perspective plane view, FIG. 1B is a sectional view taken along the line A-A of FIG. 1A, and FIG. 1C is a back view of the main part of FIG. 1A.

Figure 2:
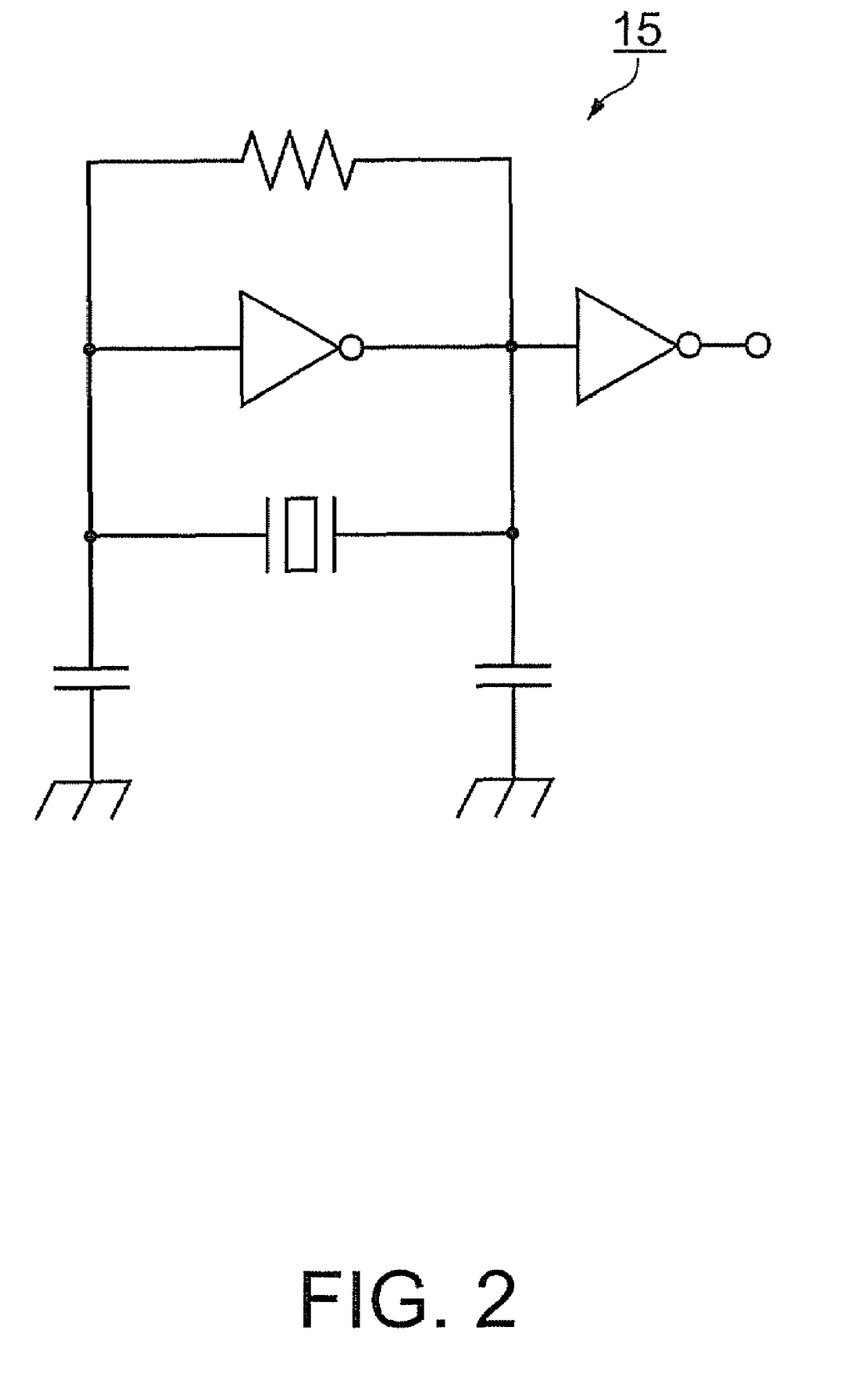
FIG. 2 is a schematic view showing a structure of an oscillation circuit of the crystal oscillator according to the first embodiment of the invention.

FIG. 2 is a schematic view showing a structure of an oscillation circuit of the crystal oscillator.

In each figure including FIGS. 1A to 1C, dimensional ratio of respective elements differs so as to clearly show the structure.

<Structure>

As shown in FIGS. 1A to 1C, this crystal oscillator 1 includes a quartz substrate 10 as a piezoelectric substrate, a package 20, a lid 21, and the like.

The quartz substrate 10 is fixed to the package 20 at a base part 12 side thereof by an adhesive 23 within the package 20. The adhesive 23 is applied to the base part 12 side so as not to disturb vibration (oscillation) of a vibrating part 11.

The lid 21 is bonded to the package 20 by a joint member 24 formed on the periphery of the package 20. Thus the inside of the package 20 is sealed air-tightly.

The quartz substrate 10 is an AT-cut quartz crystal substrate formed by cutting crystal in a direction of about 35 degrees with respect to an optical axis, and includes the vibrating part 11 and a base part 12. In this embodiment, the thickness of the quartz substrate 10 is 500 μm as a preferred example.

To a first main surface 13 in the vibrating part 11 of the quartz crystal substrate 10, a pair of excitation electrodes 14 is provided. To the base part 12, an oscillation circuit 15 is provided.

The excitation electrodes 14 and the oscillation circuit 15 are coupled by short connection electrodes 16. On a second main surface 17 in the vibrating part 11, a common electrode 18 is formed in an opposed manner to the pair of excitation electrodes 14.

Though the common electrode 18 is formed without connection, that is, formed in a floating fashion (not shown) in FIGS. 1B and 1C, the common electrode 18 may be connected to ground. In order to secure stability of the oscillation of the oscillating part 11, it is preferable to connect the common electrode 18 to the ground.

The oscillation circuit 15 includes a thin film transistor (hereinafter, referred to as a TFT (Thin Film Transistor)) that is formed by a semiconductor process of low temperature polysilicon, on the quartz substrate 10.

In a process for forming a wiring pattern of the oscillation circuit 15, the excitation electrodes 14 and the connection electrodes 16 are formed together with. The excitation electrodes 14 and the connection electrodes 16 may be formed by photolithography and etching. Examples of a material of these electrodes include: a metal thin film of gold, aluminum, tungsten, copper and the like; or a metal thin film of an alloy of these metals.

The common electrode 18 may also be formed by photolithography and etching in the same manner.

FIG. 2 is a circuit diagram showing a structure of the oscillation circuit 15 according to the first embodiment.

The oscillation circuit 15 includes two inverters, two capacitors, and one resistance. A quartz crystal resonator shown in FIG. 2 shows the vibrating part 11 including the pair of excitation electrodes 14. FIG. 2 omits a line of power supplied to the inverters.

The package 20 is made of ceramic such as a green sheet of which a thermal expansion coefficient is close to that of the quartz substrate 10. In the package 20, an internal electrode 22 is formed near the base part 12 of the quartz substrate 10 and is connected with the oscillation circuit 15 with a connecting wire 25 made of a metal such as Au or Al by wire bonding. The internal electrode 22 is coupled with an external electrode 26 that is formed on the bottom face of the package 20.

The lid 21 is made of a material of which the thermal expansion coefficient is close to that of the quartz substrate 10, such as a metal like kovar; ceramic; and glass. The lid 21 is bonded to the package 20 by the joint member 24 made of low melting glass, for example. Thus the inside of the package 20 is sealed air-tightly.

As described above, the crystal oscillator 1 is structured such that the excitation electrodes 14, the oscillation circuit 15, and the common electrode 18 are provided on the quartz substrate 10 thereof and the excitation electrodes 14 and the oscillation circuit 15 are connected by the connection electrodes 16.

The crystal oscillator 1 may have such structure that one of the excitation electrodes 14 is formed on the second main surface 17 side instead of the common electrode 18.

<Operation and Effect>

An operation and an advantageous effect of the crystal oscillator 1 structured as above will be described below.

Power is supplied to the external electrode 26 from external equipment which is not shown. The power supplied to the external electrode 26 is inputted into the oscillation circuit 15 formed on the base part 12 of the quartz substrate 10 through the internal electrode 22 and the connecting wire 25.

Thus a voltage is applied to the excitation electrodes 14 and the common electrode 18 and accordingly the vibrating part 11 generates a thickness-shear vibration.

In a case of the thickness-shear vibration of the AT cut quartz substrate, an oscillation frequency is determined by a thickness t of the vibrating part 11 of the quartz substrate 10.

In a case where a vibration mode order is n (n=1, 3, 5, 7, 9, . . . ), the relational expression is as the following.

$$\omega = 1.67 \times n/t \, (\omega: \text{MHz}, t: \text{mm}, n=1, 3, 5, 7, 9, \ldots )$$

A case where the thickness t of the vibrating part 11 of the quartz substrate 10 is 500 μm is now described as a preferred example.

In this case, an oscillation in the fundamental mode of which a vibration mode order was 1 was observed, so that the oscillation frequency was about 3.3 MHz.

Here, the oscillation frequency is not limited to 3.3 MHz, but a desired oscillation frequency can be obtained by adjusting the thickness t of the vibrating part 11.

An electric signal oscillated in the crystal oscillator 1 is outputted from the external electrode 26 coupling with an output terminal of the inverters at a subsequent stage in FIG. 2 to external equipment and the like.

As described above, since the excitation electrodes 14 and the oscillation circuit 15 are formed on the quartz substrate 10 in a single process in the crystal oscillator 1 of the first embodiment, the quartz substrate 10 including the vibrating part 11 and the oscillation circuit 15 are unified. Thus the space efficiency is enhanced and accordingly the crystal oscillator 1 can be miniaturized. Especially, since the oscillation circuit 15 is composed of the thin film mainly including the TFT, the crystal oscillator 1 does not require the discrete component as related art. Thus the crystal oscillator 1 that is thin can be provided. Further, since the vibrating part 11 of the quartz substrate 10 functions as a piezoelectric resonator element (piezoelectric resonator) in itself, the crystal oscillator 1 does not require mounting the piezoelectric resonator on a flat plate as related art, thereby being able to be thinned.

Furthermore, the crystal oscillator 1 includes the quartz substrate 10 and the oscillation circuit 15 in a unified manner and thus the number of manufacturing steps is reduced due to the reduced number of components, improving the productivity thereof.

In addition, because of the unification of the quartz substrate 10 and the oscillation circuit 15, the excitation electrodes 14 and the oscillation circuit 15 are coupled in a short distance. Therefore, electromagnetic interference such as an impedance mismatch between the connecting electrodes 16 is suppressed, improving the performance of the crystal oscillator 1.

Since the oscillation circuit 15 and the pair of excitation electrodes 14 are formed on the first main surface 13 of the quartz substrate 10, the oscillation circuit 15 and the excitation electrodes 14 are coupled by single-sided wiring, facilitating the wiring.

The oscillation circuit 15, the excitation electrodes 14, and the connection electrodes 16 can be formed in a single semiconductor process, realizing high production efficiency and excellent productivity.

Since the AT cut quartz substrate is employed as the quartz substrate 10, the crystal oscillator 1 has a frequency-temperature property of a cubic function having an inflection point around normal temperature. In addition, the frequency can be increased by thinning the thickness t of the vibrating part 11, so that a desired oscillation frequency can be obtained by setting the thickness. Thus, a high frequency oscillator having a favorable temperature property can be easily realized.

Since the vibrating part 11 of the quartz substrate 10 is air-tightly sealed in a storing space formed by the package 20 and the lid 21 in the crystal oscillator 1, the vibrating part 11 is hardly affected by exterior environment, being able to prevent the excitation electrodes 14 from deteriorating. Thus the vibrating part 11 can constantly oscillate in a stable manner.

Further, if the storing space is vacuumed or filled with an inert gas such as nitrogen, helium, and argon gas, the excitation electrodes 14 can be further prevented from deteriorating caused by the affect of the exterior environment.

The crystal oscillator 1 according to the first embodiment is applicable as a compact oscillating module mounting an oscillator.

Second Embodiment

Figure 3A:
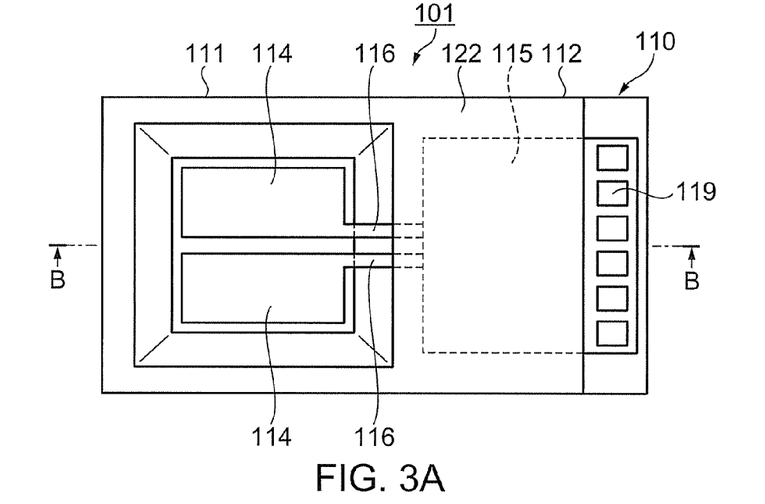
FIGS. 3A to 3C are schematic views showing a structure of a chemical sensor according to a second embodiment of the invention.
Figure 3B:
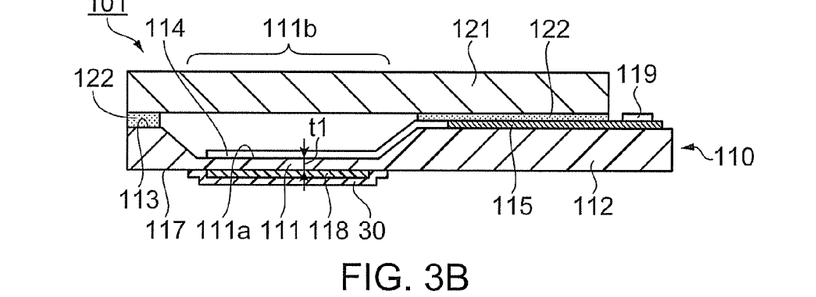
Figure 3C:
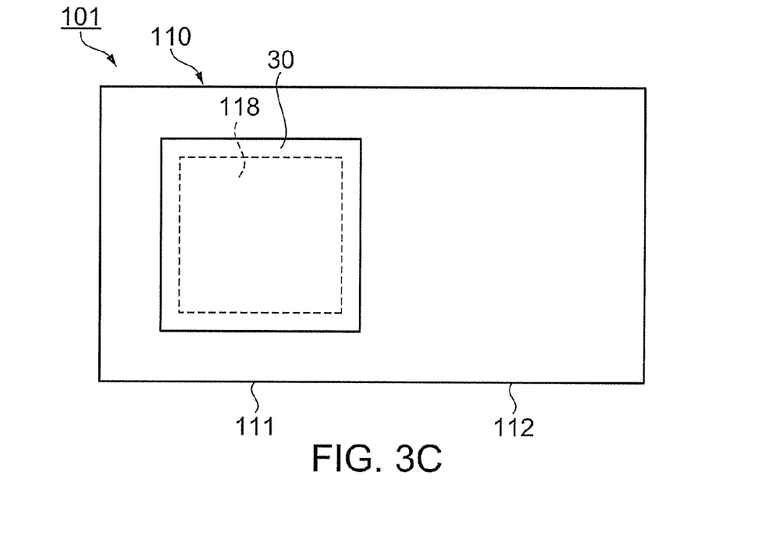

FIGS. 3A to 3C are schematic views showing a structure of a chemical sensor that detects an organic solvent molecule in vapor phase and employs a piezoelectric oscillator according to a second embodiment of the invention. FIG. 3A is a front plane view, FIG. 3B is a sectional view taken along the line B-B of FIG. 3A, and FIG. 3C is a back plane view. In FIG. 3A, some elements are omitted so as to show the drawing comprehensible.

<Structure>

As shown in FIGS. 3A to 3C, this chemical sensor 101 includes a quartz substrate 110 as a piezoelectric substrate, a sealing plate 121 as a lid member, an adhesive 122, and the like.

The chemical sensor 101 of the second embodiment includes a sensitive film 30 on its common electrode 118 provided on the quartz substrate 110 that has a similar structure to the quartz substrate 10 of the crystal oscillator 1 of the first embodiment. The quartz substrate 110 is manufactured by the semiconductor process in a similar manner to the quartz substrate 10. Differences from the first embodiment will be primarily described below.

Referring to FIG. 3B, the sealing plate 121 is fixed on a first main surface 113 of the quartz substrate 110 by the adhesive 122. The adhesive 122 is mainly applied to a base part 112 side and the periphery of the sealing plate 121 so as not to disturb vibration (oscillation) of a vibrating part 111.

The quartz substrate 110 is an AT-cut quartz substrate formed by cutting crystal in a direction of about 35 degrees with respect to an optical axis and includes the vibrating part 111 and the base part 112. In this embodiment, the thickness of the quartz crystal substrate 110 is 500 µm as a preferred example.

The vibrating part 111 has a recess on the first main surface 113 side of the quartz substrate 110. In this embodiment, the thickness t1 of the vibrating part 111 is 55 µm as a preferred example.

To the first main surface 113 in the vibrating part 111 of the quartz substrate 110, a pair of excitation electrodes 114 is provided. To the base part 112, an oscillation circuit 115 is provided. The difference of the quartz substrate 110 of this embodiment from the quartz substrate 10 of the first embodiment is that the vibrating part 111 of the quartz substrate 110 has a recess on the first main surface 113. Namely, the quartz substrate 110 has an "inverted mesa structure" in which the vibrating part 111 is thinned only around the excitation electrodes 114. The recess can be formed by photolithography or etching.

The pair of excitation electrodes 114 is formed on a bottom surface 111a of the recess formed on the vibrating part 111, and connection electrodes 116 that connect the excitation electrodes 114 and the oscillation circuit 115 are formed along an inclined surface extending from the bottom surface 111a toward the oscillation circuit 115 (refer to FIG. 3B).

On a second main surface 117 in the vibrating part 111, the common electrode 118 is formed in an opposed manner to the pair of excitation electrodes 114. The common electrode 118 may be formed in a floating manner without connection, but it is preferably coupled to the ground for the stability of oscillation of the vibrating part 111.

The oscillation circuit 115 includes a TFT formed by a semiconductor process of a low temperature polysilicon on the quartz substrate 110.

In a process for forming a wiring pattern of the oscillation circuit 115, the excitation electrodes 114 and the connection electrodes 116 are formed together with. The oscillation circuit 115 is provided with a connection terminal 119 for inputting from and outputting to external equipment.

The excitation electrodes 114 and the connection electrodes 116 may be formed by photolithography and etching. Examples of a material of these electrodes include: a metal thin film of gold, aluminum, tungsten, copper, and the like; or a metal thin film of an alloy of these metals.

The common electrode 118 may also be formed by photolithography and etching in the same manner.

On the common electrode 118, the sensitive film 30 of which a mass changes by adsorbing a selected substance is formed in a manner covering the common electrode 118.

The sensitive film 30 is formed, for example, such that a liquid obtained by diluting a component of the sensitive film with a solvent is applied with a dispenser. Alternatively, the sensitive film 30 may be formed by discharging the liquid by ink-jetting. If the component of the sensitive film is gelled, the sensitive film 30 can be formed by silk printing or tampon printing as well.

The sensitive film 30 is made of polystyrene in the present embodiment. Polystyrene adsorbs an organic solvent molecule of, for example, toluene, acetic acid, butyl acetate, acetone, acetaldehyde, propanal, methanol, ethanol, diethyl ether, and ammonia, so that the sensitive film 30 can detect these substances. The sensitive film 30 is not limited to polystyrene, but may be made of a material that selectively adsorbs other desired substance.

For example, the sensitive film 30 made of polypropylene can adsorb a molecule of toluene or xylene in a vapor phase. If the sensitive film 30 is made of polycarbonate, it can adsorb a molecule of aldehyde in a vapor phase.

The sealing plate 121 is formed in a plate shape with a material of which a thermal expansion coefficient is close to that of the quartz substrate 110, such as ceramic and glass. The sealing plate 121 seals the recess 111b and the oscillation circuit 115 provided on the first main surface 113 of the quartz substrate 110 with the adhesive 122 interposed. In this case, since the sealing plate 121 is formed in a plate shape, there is a space between the recess 111b and the sealing plate 121. The connection terminal 119 formed on the oscillation circuit 115 is exposed to outside without being sealed.

The adhesive 122 is made of an insulative adhesive such as an acrylic adhesive, an ultraviolet-curing adhesive, and low melting glass. The adhesive 122 covers the periphery of the recess 111b and the oscillation circuit 115 at the first main surface 113 side of the quartz substrate 110.

The chemical sensor 101 is structured such that the recess 111b of the quartz substrate 110 and a part of the oscillation circuit 115 are sealed by the sealing plate 121 while interposing the adhesive 122 that covers the periphery of the recess 111b and the oscillation circuit 115. The sealing plate 121 forms a space with the recess 111b therebetween.

Here, the space may be filled with an inert gas such as a nitrogen gas, or may be vacuumed.

<Operation and Effect>

An operation and an advantageous effect of the chemical sensor 101 structured as above will be described below. Power source is supplied to the connection terminal 119 from external equipment which is not shown. The power supplied to the connection terminal 119 is inputted into the oscillation circuit 115 formed on the base part 112 of the quartz substrate 110.

Thus a voltage is applied to the excitation electrodes 114 and the common electrode 118 and accordingly the vibrating part 111 generates a thickness-shear vibration. An oscillation frequency is outputted to an external measuring device as needed or regularly.

In this embodiment, the thickness t1 of the vibrating part 111 of the quartz substrate 110 is 55 μm as a preferred example.

In this case, an oscillation in the fundamental mode of which a vibration mode order was 1 was measured, so that the oscillation frequency was about 30 MHz derived by the expression described in the first embodiment.

Thus the chemical sensor 101 employs a frequency that is comparatively higher than that of the crystal oscillator 1 of the first embodiment.

If the sensitive film 30 made of polystyrene adsorbs an organic solvent molecule of alcohol or the like in a vapor phase, the mass of the sensitive film 30 increases because of the adsorption of the organic solvent molecule. The whole mass of the vibrating part 111 increases because of the increase of the mass of the sensitive film 30, so that the oscillation frequency shifts to a low frequency side.

Namely, if the shift of the oscillation frequency is detected, the presence or the contained amount of detection substance of alcohol or the like in the vapor phase can be detected.

In particular, external equipment is allowed to store a look up table (LUT) showing a relative relation between an output frequency and a contained amount of a detection substance in advance, for example, and then a frequency of an outputted signal (output frequency) from the connection terminal 119 connecting with the output terminal of an inverter at a subsequent stage of FIG. 2 is measured. The output frequency that is measured is referred to the LUT, deriving the contained amount of the detection substance. Here, the detecting method of a detection substance is not limited to the above.

Even in a case where the changing amount of the mass of the sensitive film 30 stays constant, as the thickness t1 of the vibrating part 111 becomes smaller, an affect of the mass change of the sensitive film 30 with respect to the thickness t1 of the vibrating part 111 increases, increasing the changing amount of the frequency. Therefore, the present embodiment thins the thickness t1 of the vibrating part 111 of the quartz substrate 110 up to 55 μm so as to increase the frequency, enhancing the detecting sensitivity with respect to the organic solvent molecule.

As described above, the chemical sensor 101 of the second embodiment includes the excitation electrodes 114 and the oscillation circuit 115 provided on its quartz substrate 110, and the sensitive film 30 provided on the vibrating part 111 of the quartz substrate 110. Therefore, if the mass increase of the sensitive film 30 increases due to the adsorption of the organic solvent molecule of alcohol or the like in the vapor phase, the frequency of the vibrating part 111 changes. Accordingly, the chemical sensor 101 can detect a selected substance such as alcohol in the vapor phase.

In addition, in the chemical sensor 101, the excitation electrodes 114, the oscillation circuit 115, and the sensitive film 30 are formed on the quartz substrate 110 to be unified, improving the space efficiency and miniaturization. Further, since the quartz substrate 110, the excitation electrodes 114, the oscillation circuit 115, and the sensitive film 30 are unified in the chemical sensor 101, the number of manufacturing steps is reduced due to the reduced number of components, improving the productivity.

Furthermore, according to the chemical sensor 101, because of the unification of the quartz substrate 110, the excitation electrodes 114, the oscillation circuit 115, and the sensitive film 30, the excitation electrodes 114 and the oscillation circuit 115 are coupled in a short distance. Therefore, electromagnetic interference such as an impedance mismatch between the connecting electrodes 116 is suppressed, improving the performance of the chemical sensor 101.

According to the chemical sensor 101, the oscillation circuit 115 is composed of the TFT, so that the oscillation circuit 115 can be manufactured by the semiconductor process. Thus the excitation electrodes 114 and the connecting electrode 116 can be formed together in the wiring process of the oscillation circuit 115, improving the productivity of the chemical sensor 101.

Especially, since the oscillation circuit 115 is composed of the thin film mainly including the TFT, the chemical sensor 101 does not require the discrete component as related art. Thus the chemical sensor 101 that is thin can be provided.

Further, since the vibrating part 111 of the quartz substrate 110 functions as a piezoelectric resonator element (crystal resonator) in itself, the chemical sensor 101 does not require mounting the piezoelectric resonator on a flat plate as related art, thereby being able to be thinned.

According to the chemical sensor 101, the quartz substrate 110 is the AT cut quartz substrate. Therefore the frequency can be increased by reducing the thickness of the quartz substrate 110 and the temperature property is excellent. Thus the chemical sensor 101 can widen the range of the frequency change due to the adsorption of the organic solvent molecule of alcohol or the like and suppress the amount of the frequency change due to the temperature change of the surroundings. Therefore, the detecting sensitivity and the detecting accuracy with respect to a selected substance such as alcohol improve.

According to the chemical sensor 101, the sensitive film 30 is formed in a manner covering the common electrode 118 so as to adsorb the organic solvent molecule of alcohol or the like in a wide area. Therefore, the amount of the frequency change increases, improving the detecting sensitivity.

In the chemical sensor 101, the excitation electrodes 114 are formed on the first main surface 113 side to which the oscillation circuit 115 is provided. Thus the oscillation circuit 115 and the excitation electrodes 114 are coupled by single-sided wiring, facilitating the wiring.

In the chemical sensor 101, the vibrating part 111 of the quartz substrate 110 has a recess (inverted mesa structure). Therefore, since the thickness t1 of the inside of the vibrating part 111 can be thinned without changing the thickness of the periphery of the vibrating part 111, the frequency can be increased while maintaining the strength of the quartz substrate 110. Accordingly, the amount of the frequency change due to the adsorption of the organic solvent molecule of alcohol or the like increases, improving the detecting sensitivity.

In the chemical sensor 101, the recess 111b of the quartz substrate 110 and the oscillation circuit 115 are sealed by the sealing plate 121 with the adhesive 122 interposed. Thus the chemical sensor 101 can prevent the excitation electrodes 114 in the recess 111b and the oscillation circuit 115 from contacting the vapor phase, being able to suppress performance degradation thereof. Therefore, the chemical sensor 101 does not need the package as disclosed in FIG. 4 of JP-A-2004-264255. Accordingly, the chemical sensor 101 further improves the productivity and can be miniaturized.

In the chemical sensor 101, the recess 111b of the quartz substrate 110 is sealed. Therefore, the amount of the frequency change due to the adsorption of other molecules in the vapor phase in the recess 111b is not added to the amount of the frequency change due to the adsorption of the organic solvent molecule of alcohol or the like, improving the detecting accuracy.

In the chemical sensor 101, the recess 111b of the quartz substrate 110 is sealed by the sealing plate 121 that is formed to make a space between itself and the recess 111b, so that the vibration of the vibrating part 111 is not disturbed, being able to maintain the detecting sensitivity.

In the chemical sensor 101, the space between the recess 111b of the quartz substrate 110 and the sealing plate 121 is filled with an inert gas or is vacuumed, being able to suppress the deterioration of the excitation electrodes 114.

The present embodiment applies the chemical sensor 101 for detecting the organic solvent molecule of alcohol and the like in the vapor phase, but the invention is not limited to it. The chemical sensor 101 may be applied for detecting a selected substance to be a detected target such that the component of the sensitive film 30 is appropriately set and the chemical sensor 101 is soaked in various waters such as tap water, discharged water, and aqueous solution.

In this case, the recess 111b of the vibrating part 111 of the quartz substrate 110 and the oscillation circuit 115 are sealed with the adhesive 122 and the sealing plate 121 in the chemical sensor 101. Therefore, even if the chemical sensor 101 is soaked in various liquids, the vibrating part 111 and the oscillation circuit 115 are not affected, being able to detect the selected substance.

Third Embodiment

Figure 4A:
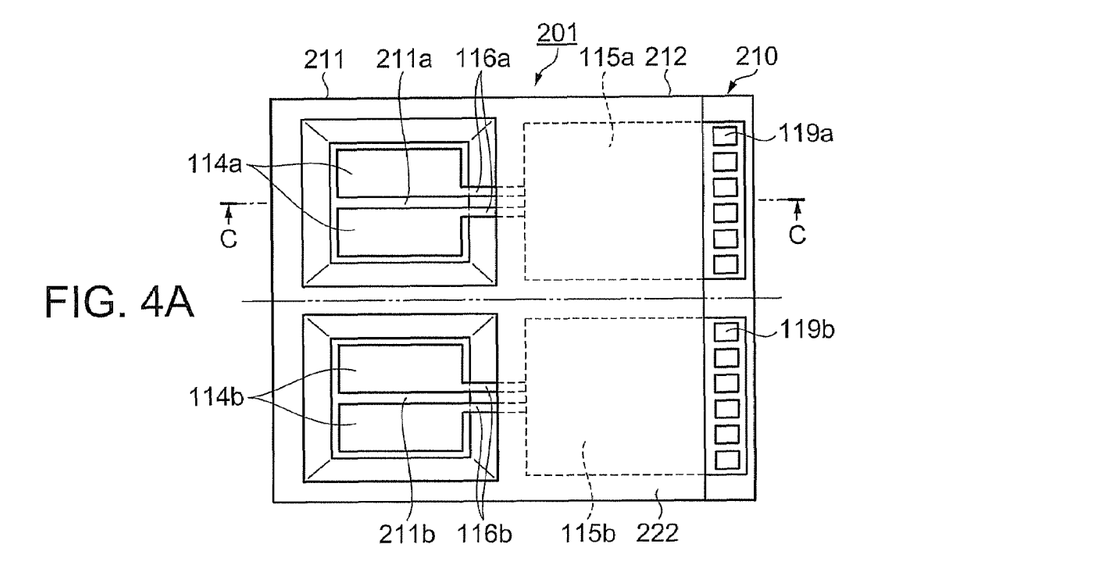
FIGS. 4A to 4C are schematic views showing a structure of a multi-sensor according to a third embodiment of the invention.
Figure 4B:
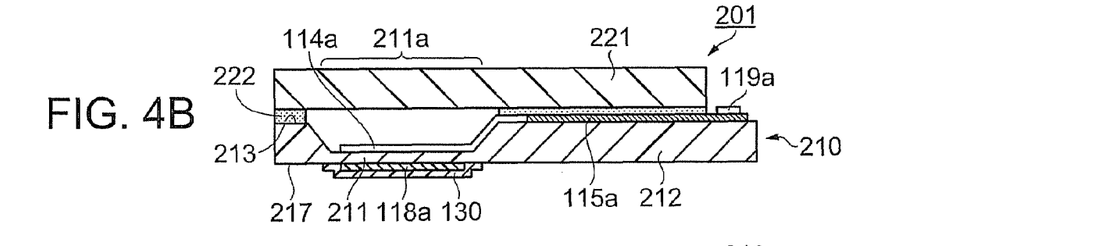
Figure 4C:
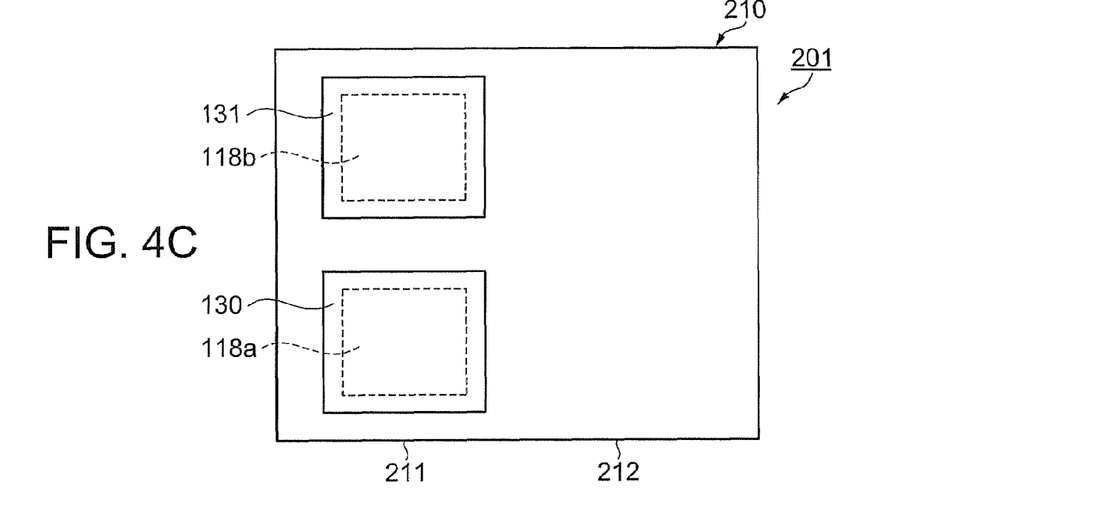

FIGS. 4A to 4C are schematic views showing a structure of a multi-sensor employing a piezoelectric oscillator according to a third embodiment of the invention. The multi-sensor includes a plurality of chemical sensors that detect a molecule in vapor phase and are provided on a quarts substrate as a large format piezoelectric substrate.

FIG. 4A is a front plane view, FIG. 4B is a sectional view taken along the line C-C of FIG. 4A, and FIG. 4C is a back plane view. In FIG. 4A, some elements are omitted so as to show the drawing comprehensible.

<Structure>

As shown in FIGS. 4A to 4C, this multi-sensor 201 of the third embodiment includes two chemical sensors 101 of the second embodiment provided to one quartz substrate 210. Therefore, differences from the second embodiment will be primarily described below.

The multi-sensor 201 includes the quartz substrate 210 that is an AT cut quartz substrate. The quartz substrate 210 is provided with two recesses 211a, 211b (inverted mesa structure), two excitation electrodes 114a, 114b, and two common electrodes 118a, 118b on its vibrating part 211; and two oscillation circuits 115a, 115b on its base part 212.

In terms of the two excitation electrodes 114a, 114b and two oscillation circuits 115a, 115b, the excitation electrode 114a is coupled with the oscillation circuit 115a by a connection electrode 116a, and the excitation electrode 114b is coupled with the oscillation circuit 115b by a connection electrode 116b.

In the multi-sensor 201, recesses 211a, 211b, and the oscillation circuits 115a, 115b that are provided to a first main surface 213 of the quartz substrate 210 are sealed by a sealing plate 221 with an adhesive 222 interposed. The adhesive 222 is interposed to cover peripheries of the recesses 211a, 211b and the oscillation circuits 115a, 115b. Between the sealing plate 221 and the recesses 221a, 221b, spaces are formed. In this case, connecting terminals 119a, 119b are exposed to outside.

The difference of the third embodiment from the second embodiment is that the multi-sensor 201 is provided with a sensitive film 130 formed to cover the common electrode 118a and with a sensitive film 131 formed to cover the common electrode 118b on a second main surface 217 of the quartz substrate 210.

The sensitive film 130 is made of polypropylene in this embodiment. Polypropylene adsorbs a molecule of toluene, xylene, and the like in a vapor phase.

The sensitive film 131 is made of polycarbonate. Polycarbonate adsorbs a molecule of acetaldehyde in a vapor phase.

The multi-sensor 201 may be cut along a two-dot chain line in FIG. 4A to be separated into two chemical sensors.

The sealing plate 221 may be divided into two in advance.

<Operation and Effect>

Figure 5:
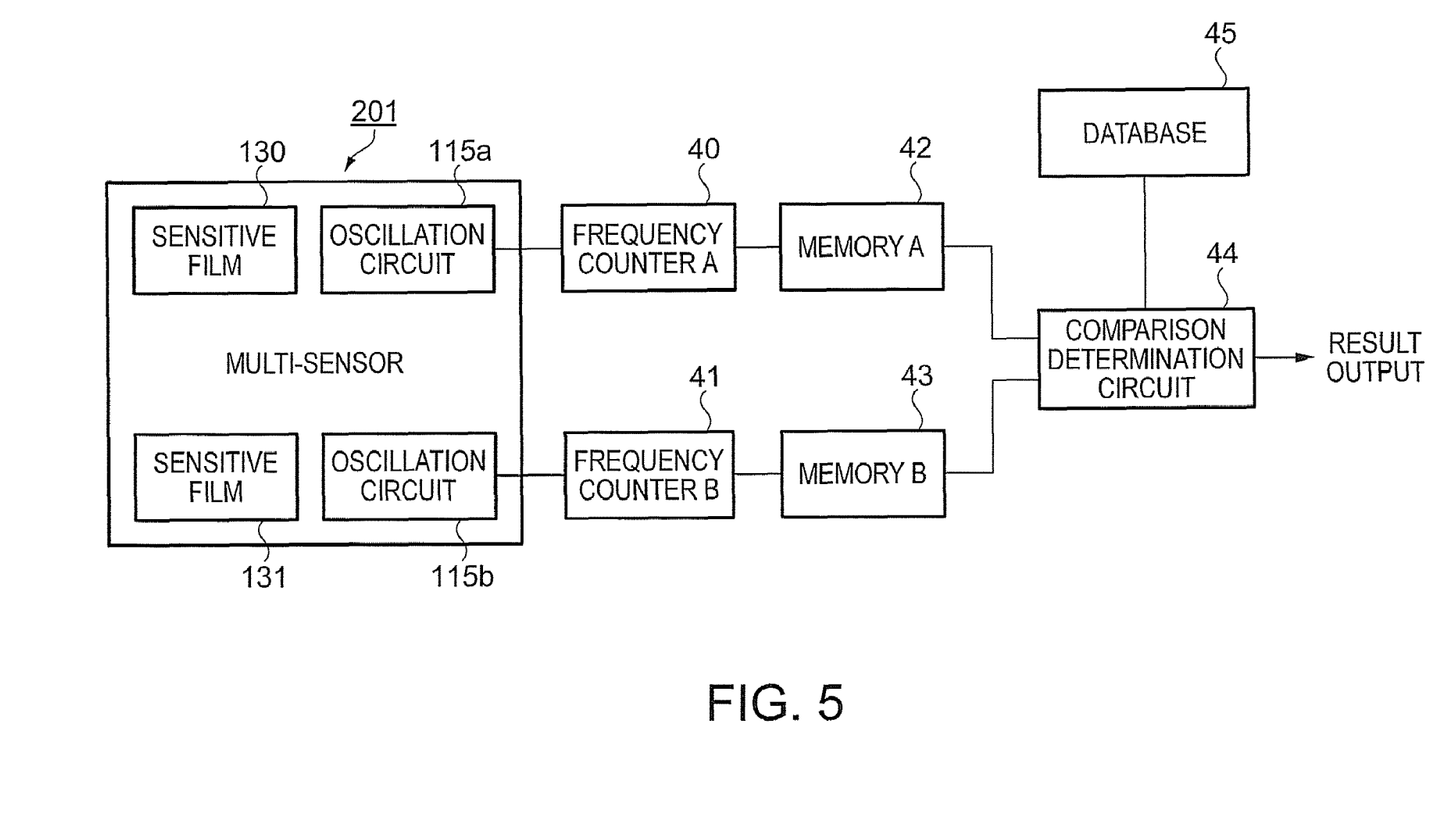
FIG. 5 is a block diagram of a control circuit of the multi-sensor according to the third embodiment of the invention.

An operation and an advantageous effect of the multi-sensor 201 structured as above will be described with reference to FIGS. 4A to 5. FIG. 5 is a block diagram showing an example of a control circuit controlling the multi-sensor 201 of the present embodiment.

Power source is supplied to the connection terminals 119a, 119b from external equipment which is not shown. The power supplied to the connection terminals 119a, 119b is inputted into the oscillation circuits 115a, 115b formed on the base part 112 of the quartz substrate 210.

Thus a voltage is applied to the excitation electrodes 114a, 114b and the common electrodes 118a, 118b and accordingly the vibrating part 211 generates a thickness-shear vibration. At this point, the oscillation frequencies are respectively measured as needed or regularly by a frequency counter A 40 and a frequency counter B 41 that are respectively coupled through the connection terminals 119a, 119b to the oscillation circuits 115a, 115b, and then stored in a memory A 42 and a memory B 43.

Subsequently, the sensitive film 130 made of polypropylene adsorbs a molecule of toluene in a vapor phase and the sensitive film 131 made of polycarbonate adsorbs a molecule of acetaldehyde in the vapor phase.

Then the mass of the sensitive film 130 increases correspondingly to the molecule of toluene adsorbed and the mass of the sensitive film 131 increases correspondingly to the molecule of acetaldehyde adsorbed.

Because of the increase of the mass of the sensitive films 130 and 131, the oscillation frequencies of the recesses 211a and 211b in the vibrating part 211 respectively shift to a lower frequency side.

At this point, the oscillation frequencies that have shifted to the lower frequency side are respectively measured at the frequency counter A 40 and the frequency counter B 41 and then respectively stored in the memories A 43 and B 43.

Thus a comparison determination circuit 44 detects the changing amount over aging of the frequencies stored in the memory A 42 and the memory B 43 and then refers characteristics of the changing amount to a database 45 so as to output detecting results of toluene and acetaldehyde in the vapor phase.

The database 45 may be allowed to store a look up table (LUT) showing a relative relation between an output frequency and containing amount of each detection substance of each of the sensitive films 130 and 131.

Thus not only the presence of toluene and acetaldehyde in the vapor phase but also the respective containing amounts can be detected.

As described above, the multi-sensor 201 of the third embodiment has the following advantageous effects as well as those described in the second embodiment.

The multi-sensor 201 includes two excitation electrodes 114a, 114b, two oscillation circuits 115a, 115b, two common electrodes 118a, 118b, and two sensitive films 130, 131 that are provided on one quartz substrate 210. Thus the multi-sensor 201 in which two sensors are formed on one quartz substrate 210 can be obtained.

The multi-sensor 201 includes different kinds of sensitive films 130 and 131. Therefore, the sensitive films 130 and 131 respectively can adsorb different substances. Accordingly, a miniaturized multi-sensor that detects two selected substances by two sensors provided to one quartz substrate 210 can be obtained.

According to the multi-sensor 201, two sensors can be manufactured at a time by dividing one quartz substrate 210 after the sensors are formed thereon, improving the productivity.

The third embodiment describes the multi-sensor 201 including two sensors, the invention is not limited to this. The multi-sensor 201 may include three, four, or more of sensors on one quartz substrate 210. Accordingly, a plurality of substances can be detected by one multi-sensor.

Alternatively, a multi-sensor including a plurality of sensors may be provided with a plurality of sensitive films made of the same material. By this multi-sensor, a specific substance can be more accurately detected. In particular, the multi-sensor is provided with a plurality of sensors that have sensitive films corresponding to a substance to be especially detected. By this multi-sensor, an average value of detected frequencies of the plurality of sensitive films can be derived, for example. Thus, the detecting accuracy is enhanced. In addition, even if one sensor is broken, the presence of the substance can be securely detected by deriving the average value. If the sensitive films are placed diagonally, for example, in the multi-sensor, a containing amount of the substance in each place can be detected.

While the oscillation circuit 15, the excitation electrodes 14, and the connection electrodes 16 are formed on the quartz substrate 10 by the low temperature poly-silicon semiconductor process in the first embodiment, the invention is not limited to this.

The semiconductor process is suitable as long as each of the components, including the oscillation circuit 15, can be formed on the quartz substrate 10 in the process. The semiconductor process may be a combination, for example, of a photolithography technique, an etching technique, a thin film forming technique, and the like. This is same in the second and third embodiments.

While the first embodiment describes that the oscillation circuit 15 oscillates shown in FIG. 2 a single frequency when power source is applied thereto, the invention is not limited to this.

The oscillation circuit 15 is suitable as long as it can be formed by a predetermined semiconductor process of a low temperature polysilicon on the quartz substrate 10. Alternatively, the oscillation circuit 15 may include a dividing circuit or a phase locked loop (PLL) circuit, for example. In this structure, a higher frequency can be easily obtained and the crystal oscillator 1 in which an output frequency can be programmed can be obtained. This is same in the second and third embodiments.

The chemical sensor 101 of the second embodiment and the multi-sensor 201 of the third embodiment are applicable to an odor sensor, a gas sensor, a biosensor, and the like as well as to the chemical sensor.

What is claimed is:

1. A piezoelectric oscillator, comprising:
   a piezoelectric substrate having at least a vibrating part and a base part;
   an excitation electrode formed on the vibrating part; and
   an oscillation circuit formed on the base part, wherein
   the oscillation circuit includes a thin film transistor made of one of polysilicon and monocrystalline silicon and is coupled to the excitation electrode.

2. The piezoelectric oscillator according to claim 1, wherein the piezoelectric substrate is an AT cut quartz substrate.

3. The piezoelectric oscillator according to claim 1, wherein the oscillation circuit and the excitation electrode are formed on a first main surface of the piezoelectric substrate, and a common electrode is formed on a second main surface in an opposed manner to the excitation electrode.

4. The piezoelectric oscillator according to claim 1, wherein the vibrating part of the piezoelectric substrate has a recess on the first main surface.

5. A sensor, comprising:
   a piezoelectric substrate having at least a vibrating part and a base part;
   an excitation electrode formed on the vibrating part;
   an oscillation circuit formed on the base part; and
   a sensitive film formed on the vibrating part and increasing a mass thereof by adsorbing a selected substance, wherein
   the oscillation circuit includes a thin film transistor made of one of polysilicon and monocrystalline silicon and is coupled to the excitation electrode.

6. The sensor according to claim 5, wherein the piezoelectric substrate is an AT cut quartz substrate.

7. The sensor according to claim 5, wherein the oscillation circuit and the excitation electrode are formed on a first main surface of the piezoelectric substrate, a common electrode is formed on a second main surface in an opposed manner to the excitation electrode, and the sensitive film is formed so as to cover the common electrode.

8. The sensor according to claim 5, wherein the vibrating part has a recess on the first main surface.

9. The sensor according to claim 8, further comprising:
   a lid member for protecting the piezoelectric substrate, wherein the lid member covers the vibrating part and a part of the oscillation circuit and is bonded to the piezoelectric substrate at least a periphery thereof, and a space formed by the lid member and the recess of the vibrating part is sealed.

10. The sensor according to claim 5, wherein a connection terminal, the connection terminal being for inputting from and outputting to outside, of the oscillation circuit is exposed.

11. A multi-sensor, comprising:
    a plurality of sensors according to claim 5 on a large format piezoelectric substrate.

12. The multi-sensor according to claim 11, wherein each of the plurality of sensors includes the sensitive film, the sensitive film includes a plurality of sensitive films, and the plurality of the sensitive films selectively adsorb different substances from each other.

13. The multi-sensor according to claim 11, wherein each of the plurality of sensors includes the sensitive film, the sensitive film includes a plurality of sensitive films, and at least one of the plurality of the sensitive films selectively adsorbs a substance that is different from a substance adsorbed by the remaining ones of the plurality of sensitive films.

* * * * *